United States Patent
Pearce et al.

(10) Patent No.: US 9,359,426 B2
(45) Date of Patent: Jun. 7, 2016

(54) METHOD OF PREPARING LOW-IRON LACTOFERRIN

(75) Inventors: Kevin Neil Pearce, Hokitika (NZ); Shaojiang Chen, Hokitika (NZ)

(73) Assignee: WESTLAND CO-OPERATIVE DIARY COMPANY LIMITED, Hokitika (NL)

( * ) Notice: Subject to any disclaimer, the term of this patent is extended or adjusted under 35 U.S.C. 154(b) by 902 days.

(21) Appl. No.: 13/266,020

(22) PCT Filed: Apr. 23, 2010

(86) PCT No.: PCT/NZ2010/000079
§ 371 (c)(1),
(2), (4) Date: Jan. 5, 2012

(87) PCT Pub. No.: WO2010/123386
PCT Pub. Date: Oct. 28, 2010

(65) Prior Publication Data
US 2012/0101263 A1 Apr. 26, 2012

(30) Foreign Application Priority Data
Apr. 24, 2009 (NZ) ........................ 576456

(51) Int. Cl.
*C07K 14/79* (2006.01)
*A23J 3/08* (2006.01)
*A23J 3/32* (2006.01)
*A61K 38/00* (2006.01)

(52) U.S. Cl.
CPC . *C07K 14/79* (2013.01); *A23J 3/08* (2013.01); *A23J 3/32* (2013.01); *A23V 2002/00* (2013.01); *A61K 38/00* (2013.01)

(58) Field of Classification Search
CPC .............. C07K 14/79; A23J 3/08; A23J 3/32
See application file for complete search history.

(56) References Cited

U.S. PATENT DOCUMENTS

| | | | |
|---|---|---|---|
| 5,389,611 A * | 2/1995 | Tomita et al. ................ | 424/439 |
| 6,172,040 B1 | 1/2001 | Naidu | |
| 7,125,963 B2 | 10/2006 | Naidu | |
| 7,326,775 B2 | 2/2008 | Naidu | |
| 2006/0189790 A1 | 8/2006 | Ropp et al. | |
| 2007/0085059 A1 | 4/2007 | Mora-Gutierrez | |
| 2007/0161541 A1 | 7/2007 | Kruzel | |
| 2009/0029921 A1 | 1/2009 | Ward et al. | |

FOREIGN PATENT DOCUMENTS

| JP | 05-178759 A | 7/1993 |
|---|---|---|
| WO | 98/06424 A1 | 2/1998 |
| WO | 00/72874 A1 | 7/2000 |
| WO | WO2006/119644 | 11/2006 |

OTHER PUBLICATIONS

Teuwissen, B., et al. 1972 Eur J Biochem 31: 239-245.*
Nunes, R., et al. 1984 Biochemical and Biophysical Communications 125(2): 824-830.*
Sanchez, L., et al. 1992 Archives of Disease in Childhood 67: 657-661.*
Aisen et al., "Lactoferrin and transferrin: a comparative study", Biochim. Biophys. Acta (1972), 257 (2), pp. 314-323.
Batish VK. et al., "Antibacterial activity of Lf against some common food-borne pathogenic organisms", Aust. J. Dairy Technol. (1988) 43 (1), pp. 16-18.
Bishop, J.G. et al., "In vitro growth inhibition of mastitis-causing coliform bacteria by bovine apo-lactoferrin and reversal of inhibition by citrate and high concentrations of apo-lactoferin", Infect. Immun. (1976), 14 (4), pp. 911-918.
Chung, TDY et al., "Lactoferrin: The role of conformational changes in its iron binding and release", J. Am. Chem. Soc. (1993), 115 (15), pp. 6765-6768.
Dubois, M. et al., "Colorimetric method for determination of sugars and related substances", (1956) Anal. Chem. 28 (3), pp. 350-356.
Ellison, RT 3rd et al., "Damage of the outer membrane of enteric Gram-negative bacteria by lactoferrin and transferrin", Infect. Immun. (1988), 56 (11), pp. 2774-2781.
Ellison, RT 3rd et al., "Lactoferrin and transferrin damage of the Gram-negative outer membrane is modulated by Ca2+ and Mg2+", J. Gen. Microbiol. (1990), Jul.: 136 (7), pp. 1437-1446.
Ellison, RT 3rd et al., "Killing of Gram-negative bacteria by lactoferrin and lysozyme", J. Clin. Invest. Oct. 1991:88 (4), pp. 1080-1091.
Franken KL et al., "Purification of his-tagged proteins by immobilized chelate affinity chromatography: the benefits from the use of organic solvent", Protein Expr Purif. (2000), 18 (1), pp. 95-99.
Groves, ML, "The isolation of a red protein from milk", J. Am. Chem. Soc. (1960), 82 (13), pp. 3345-3350.
Korhonen, H, "Antimicrobial factors in bovine colostrum", Journal of the Scientific Agricultural Society of Finland (1977), 49 (5), pp. 434-447.
Kretchmar Nguyen, SA et al., "Transferrin: the role of conformational changes in iron removal by chelators". J. Am. Chem. Soc. (1993), 115 (15), pp. 6758-6764.
Law, BA et al., "The isolation and bacteriostatic properties of Lactoferrin from bovine milk whey", J. Dairy Res. (1977), 44 (3), pp. 595-599.
Magalhaes, PO et al. "Methods of endotoxin removal from biological preparations: a review", J. Pharm. Sci. (2007), 10 (3), pp. 388-404.
Masson, PL et al., "Metal-combining properties of human lactoferrin (red milk protein). 1. The involvement of bicarbonate in the reaction", European J. Biochem. (1968), 6 (4), pp. 579-584.
Petsch, D et al., "Endotoxin removal from protein solutions", J Biotechnol. (2000), 76 (2-3), pp. 97-119.
Peterson, NA et al., "Crystal structure and iron-binding properties of the R210K mutant of the N-lobe of human lactoferrin: implications for iron release from transferrins", Biochemistry (2000), 39 (22), pp. 6625-6633.

(Continued)

*Primary Examiner* — Marsha Tsay
(74) *Attorney, Agent, or Firm* — Vedder Price P.C.; Thomas J. Kowalski; Deborah L. Lu

(57) ABSTRACT

The present invention relates to methods for producing low-iron Lf having improved antimicrobial activity and to a low-iron Lf having improved antimicrobial activity.

26 Claims, 2 Drawing Sheets

(56) References Cited

OTHER PUBLICATIONS

Figure 1:
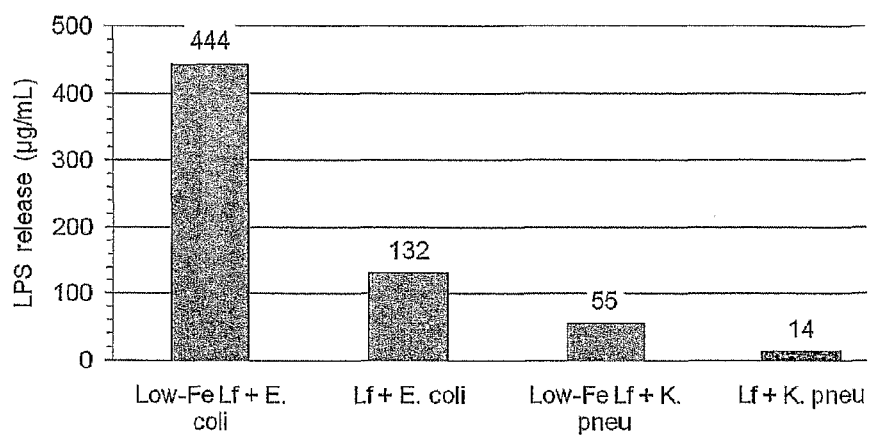

Reiter, B., "Protective proteins in milk—biological significance and exploitation", IDF Bull. Int. Dairy Fed, Brussels, Belgium (1985), 191, pp. 8-10.

Yamauchi K et al., "Antibacterial activity of lactoferrin and a pepsin-derived lactoferrin peptide fragment", Infect Immun. Feb. 1993:61(2), pp. 719-728.

Feng, M-H, et al., "Iron(III)-Chelating Resins. 3.1 Synthesis, Iron(III)-Chelating Properties, and in Vitro Antibacterial Activity of Compounds Containing 3-Hydroxy-2-methyl-4(1H)-pyridinone Ligands", J. Med. Chem (1993), vol. 36, pp. 2822-2827.

Feng, M, et al., "Preparation of Apolactoferrin with a very low saturation", J. of Dairy Science (1995), vol. 78, pp. 2352-2357.

Kontoghiorghes, G.J. iron mobilisation from lactoferrin by chelators at physiological pH, Biochimica et Biophysica Acta (1986), vol. 882, pp. 267-270.

Mazurier, J. et al., "Comparative study of the iron-binding properties of human transferrins", Biochimica et Biophysica Acta (1980), vol. 629, pp. 399-408.

Payne, K.D. et al., "Influence of Bovine Lactoferrin on the Growth of Listeria monocytogenes", J. of Food Protection (1990), vol. 53:6, pp. 468-472.

* cited by examiner

METHOD OF PREPARING LOW-IRON LACTOFERRIN

CROSS REFERENCE TO RELATED APPLICATIONS

This application is the a 371 of International Patent Application Number PCT/NZ2010/000079, filed Apr. 23, 2010, which claims priority to New Zealand Patent Application No. 576456, filed Apr. 24, 2009, both of which are incorporated herein by reference in their entirety.

FIELD OF THE INVENTION

The present invention relates to a method of preparing low-iron lactoferrin (Lf), the low-iron Lf having greater anti-microbial activity than standard Lf.

BACKGROUND OF THE INVENTION

Milk provides essential nutrients to the newborn mammal. It also contains bioactive components for the management of gastrointestinal and other bodily functions, and for defense against microorganisms that can impact on health.

Lf is one of several bioactive components present in milk and colostrum. It is also present in most exocrine fluids, including tears and saliva. Lf has multiple biological roles including regulation of iron metabolism, immune function and embryonic development. Lf has anti-microbial activity against a range of pathogens including Gram-positive and Gram-negative bacteria, yeasts and fungi. The anti-microbial activity of Lf is due in part to its ability to bind the iron essential for the growth of certain bacteria. Lf also exerts bactericidal activity by binding to lipopolysaccharide (LPS) on bacterial membranes so disrupting the cell wall (Ellison et al, 1988). LPS are hydrophobic, negatively charged molecules also known as endotoxins. Lf may scavenge LPS from its environment during its isolation. Methods have been found to remove LPS from protein preparations (Franken at al, 2000; Petsch and Anspach, 2000; Ropp and Murray, 2006; Magalhaes et al, 2007) and from Lf (Rowe et al, 2006; Naidu, 2006 & 2008; Ward at al, 2009).

Lf has been proposed for use as an antimicrobial agent in the dairy and meat industries (Payne et al, 1990; Naidu, 2001). Natural Lf is partially saturated with iron (Reiter, 1985). Some researchers (Bishop et al, 1976; Korhonen, 1977; Payne et al, 1990.) reported that the antimicrobial activity of Lf depends on its iron saturation. Batish et al, (1988) found that the antibacterial activity of apo-Lf is greater than that of natural Lf and others have confirmed this.

Lf is an iron-binding glycoprotein with one iron-binding site in an N-terminus lobe and another in a C-terminus lobe. One molecule of Lf has the ability to bind reversibly to two high-spin $Fe^{3+}$ ions in coordination with carbonate ions.

Domain opening is almost certainly the essential feature of iron release from Lf. There are three factors that trigger this process: i) interaction with specific Lf receptors, ii) reduction of the bound $Fe^{3+}$ to $Fe^{2+}$, and iii) reduced pH. Iron can be released from Lf by using water-soluble iron chelators and low pH (Groves, 1960; Masson and Heremans, 1968; Law and Reiter, 1977; Mazurier and Spik, 1980; Chung and Raymond, 1993; Feng, van der Does and Bantjes, 1993). However, completely removing iron is difficult and the iron saturation of apo-Lf is usually >10% (Batish et al, 1988; Payne et al, 1990; Chung and Raymond, 1993). Kontoghiorghes (1986) could not completely mobilize iron from Lf with any of a wide variety of soluble iron chelators at physiological pH due to the high affinity of Lf for iron (Aisen and Leibman, 1972; Chung and Raymond, 1993; Kretchmar Nguyen, Craig and Raymond, 1993). Some researchers used insoluble resins to chelate iron at pH<4 to prepare apo-Lf, but the apo-Lf still had an iron saturation of about 15% (Payne et al, 1990; Chung and Raymond, 1993). Although Feng, van der Does and Bantjes (1995) successfully removed iron from Lf with iron-chelating resin at physiological pH in the presence of citrate and other buffers, the method is complex, slow and the low Lf concentration used, which makes the process impractical for commercial use. Peterson at al (2000) showed that iron release does not begin until pH 3.5. Furthermore, because the iron removal processes were usually performed at pH<3.5 this lead to the development of turbidity in the solutions because of protein precipitation (Chung and Raymond, 1993). Modification of the conformation of the protein was sometimes observed (Mazurier and Spik, 1980).

OBJECT OF THE INVENTION

It is an object of the invention to provide a method for manufacturing low-iron Lf, or at least to provide the public with a useful choice.

SUMMARY OF THE INVENTION

The invention in a first aspect provides a method for manufacturing low-iron Lf having improved antimicrobial activity from an aqueous Lf preparation, the method including the use of a water-miscible solvent and a suitable acid such that the pH is below about 4.5, followed by removal of the iron, water-miscible solvent and acid.

Preferably the suitable acid is any one or more of citric acid, tartaric acid, oxalic acid, nitrilotriacetic acid, or EDTA plus an acid, such as, HCl, $H_2SO_4$ to adjust it to the preferred pH.

Preferably the most suitable acid is citric acid.

Preferably the suitable acid can be formed from a citric acid salt and one or more organic or inorganic acid.

Preferably the organic or inorganic acid/s is/are selected from HCl, $H_2SO_4$, acetic acid, or the like.

Preferably the citric acid salt is sodium citrate, potassium citrate or the like.

Preferably the pH is between 2.5 and about 4.5, more preferably between about 3.8 and about 4.5, most preferably between about 3.9 and about 4.2.

Preferably the water-miscible solvent is an alcohol solvent.

Preferably the water-miscible solvent is selected from methanol, ethanol, propanol, or similar solvents.

Preferably the iron, water miscible solvent and acid are removed using ultrafiltration (UF), diafiltration (DF), and/or similar conventional means.

Preferably the low-iron Lf produced contains less than 14 mg/100 g iron or 10% iron saturation.

In a second aspect the invention provides a method for manufacturing low-iron Lf, preferably containing less than 14 mg/100 g iron or 10% iron saturation, and with higher antimicrobial activity than normal commercial Lf, the said method comprising:

a) mixing an aqueous Lf preparation with an alcohol solvent and sufficient acid solution such that the pH is lowered to 2.5-4.5 to release the iron from the Lf in the aqueous Lf preparation;

b) removing the released iron, acid and alcohol by UF and/or DF to achieve a processing pH>about 5.5 and a conductivity <about 2 mS in the product;

c) further processing the low-iron Lf product produced in (b) to produce a liquid or dried low-iron Lf product.

Preferably the low-iron Lf product in step c) is freeze-dried or spray-dried.

Preferably the acid is selected from citric acid, tartaric acid, oxalic acid, nitrilotriacetic acid, or EDTA, or a citric acid salt together with an organic or inorganic acid.

Preferably the pH in step a) is lowered to between about 3.5 and about 4.5, more preferably between about 3.9 and about 4.2.

Preferably the aqueous Lf preparation in step a) is treated with acid solution for a period from about 2 hours to about 3 days to release the iron, more preferably between about 3 hours and about 24 hours, more preferably between about 5 hours and about 12 hours, most preferably between about 6 hours and about 10 hours.

Preferably the concentration of the acid solution used in step a) is between about 5-20%, most preferably about 10%.

Preferably the alcohol solvent is added prior the addition of the acid.

Preferably the alcohol solvent is selected from any one or more of methanol, ethanol, propanol or similar alcohol, more preferably the alcohol is ethanol.

Preferably the alcohol solvent is added in an amount of between about 0.2 and about 2.5% of the Lf preparation, more preferably between about 0.5 and about 1.5%, most preferably about 1%.

Preferably the processing pH is between about 3.5 and about 4.5.

Preferably the temperature in step a) is between about 2 and about 30° C.

Preferably the temperature in step b) is between about 5 and about 10° C.

Preferably the Lf in the aqueous Lf preparation is from colostrum, skim milk or whey of bovine, human and other mammals.

Preferably the Lf in the aqueous Lf preparation is isolated by any conventional method, such as by chromatograph, ion-exchanger and molecular-sieve from laboratory and commercial available Lf.

Preferably the Lf in the aqueous Lf preparation can be an undried extract or solution, or a dried powder.

Preferably the concentration of Lf in the aqueous Lf preparation is between about 0.01 and about 35% wt/vol, preferably between about 5 and about 25% wt/vol, and most preferably between about 10 and about 20% wt/vol.

In a third aspect the invention provides a low-iron Lf when produced according to either the first or second aspects of the invention.

In a fourth aspect the invention provides method of improving the anti-microbial properties of a product including a standard Lf component, the method including the step of replacing, at least in part, the standard Lf with low-iron Lf.

Preferably the low-iron Lf of the third or fourth aspects of the invention contains less than about 14 mg/100 g iron or about 10% iron saturation.

In a fifth aspect the invention provides a product when produced according to the fourth aspect of the invention.

DRAWINGS

Figure 2:
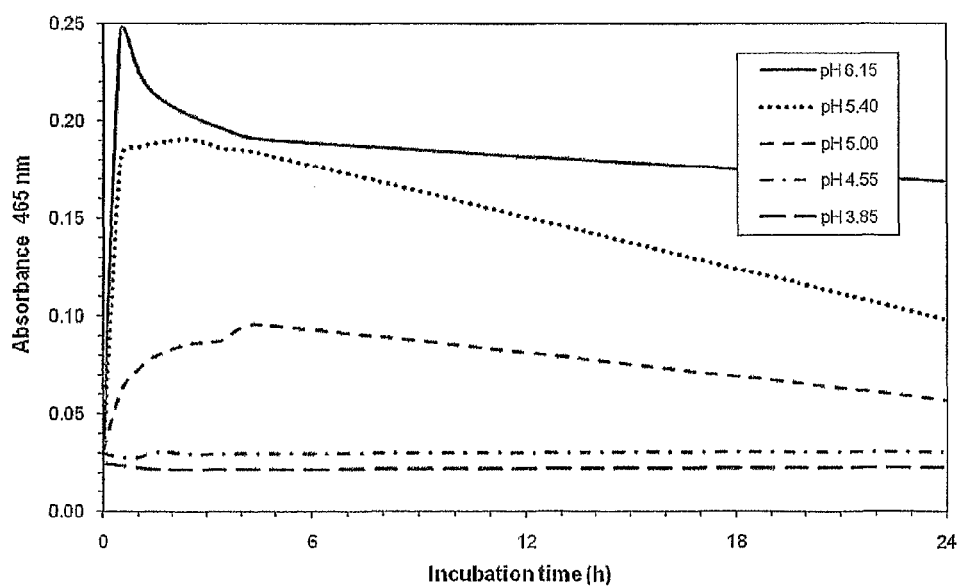
Figure 3:
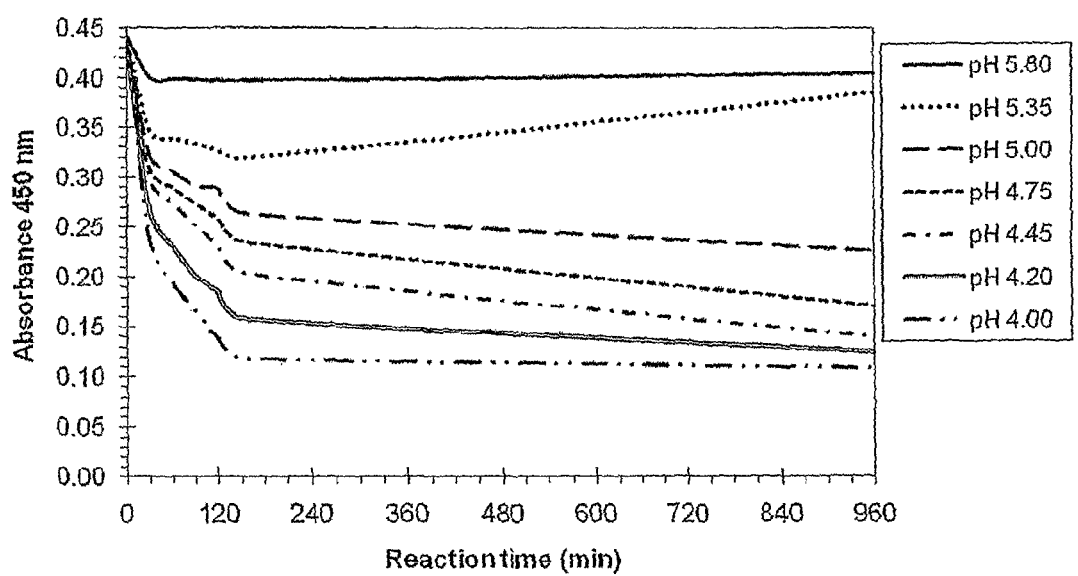

FIG. 1: shows LPS released from *E. coli* or *K. pneumoniae* incubated with different Lf preparations;

FIG. 2: shows the iron release at different pH in the present invention;

FIG. 3: relates to the iron rebinding back to Lf at different pH in this process, which affects the final product iron saturation.

ABBREVIATIONS cfu: colony forming unit
DF: diafiltration
HPLC: high performance liquid chromatography
Lf: lactoferrin
LPS: lipopolysaccharide
NZRM: New Zealand Reference Culture Collection, Medical Section
UF: ultrafiltration
XRF: X-ray fluorescence

DETAILED DESCRIPTION OF THE INVENTION

The present invention provides a method for preparing a low-iron Lf with improved antimicrobial activity, and also provides a method of improving the antimicrobial activity of products that include Lf by replacing the use of standard Lf in such products with a low-iron Lf.

Using the process according to the invention (acid+alcohol), a low-iron Lf can be produced at a mild pH (e.g. 3.8-4.5). Furthermore, a lower pH (e.g. <about 3.5) can also be used, as Lf denaturation can be reduced in the course of the preferred process. Such a process provides benefits to the user as the process is relatively simple and cost effective.

Surprisingly and importantly, the inventors have found that low-iron Lf produced by the process has a greatly improved antimicrobial activity in comparison to standard commercially available Lf. As a result, the antimicrobial activity of products that include Lf can be improved by replacing, at least in part, standard Lf in such products with low-iron Lf.

The low-iron Lf can be prepared from either laboratory or commercial Lf extracts or preparations, using a water-miscible solvent, such as alcohol solvents (e.g. methanol, ethanol or similar), in combination with a suitable acid, such as citric acid, tartaric acid, oxalic acid, nitrilotriacetic acid, or EDTA, or a citric acid salt together with an organic or inorganic acid, to remove the iron. The pH is relatively mild (e.g. below about 4.5, preferably between about 2.5 and about 4.5). This is then followed by removal of the iron and added solvent and acid using conventional means, such as UF and/or DF, and recovering the product also using conventional means, such as freeze-, spray-, or otherwise drying the product.

The low iron Lf produced by the process shows an increased antimicrobial activity in comparison to standard Lf, and has an iron content of less than about 14 mg/100 g iron or about 10% iron saturation. More preferably the iron saturation is less than about 9%.

The Lf preparations used with the present invention include Lf from colostrum, milk and whey of bovine, human or another mammal. The Lf is isolated from that source by any conventional method such as by chromatograph, ion-exchanger and molecular-sieve at either laboratory or commercial scale.

The present invention makes use of the fact that Lf can release the bound iron in a fully reversible manner, on exposure to mild pH (below about 4.5) with a proper chelator (citric acid is the preferred agent) and a suitable water miscible solvent (an alcohol solvent such as ethanol is the most preferred). Furthermore, the addition of the suitable water miscible solvent (e.g. alcohol) can prevent denaturation of Lf if a low pH 2.5-3.8 used. It is preferred that Lf is treated with a food grade acid alone or mixtures of food grade acids and also with food grade water miscible solvent (e.g. alcoholic reagents). Food grade is used due to relatively high purity, to reduce any effect on the final product. This is followed by removing the iron released from the Lf, and also the process aids (acid and water miscible solvent), by UF and DF, then freeze-, spray-, or otherwise drying the product, to produce a final low iron Lf product.

Iron Release

The Lf preparation for treatment is prepared by dissolving Lf powder in water. Alternatively, a freshly prepared aqueous extract can be used directly.

It is known that iron can be released from the Lf solution by mixing citric acid solution and Lf solution carried out at a pH<3.5 (e.g. Peterson at al, 2000) while a number of patents and papers report use of pH 2. Under such iron release conditions, especially low pH, a cloudy solution may be formed due to aggregation or denaturation of the protein (Mazurier and Spik, 1980; Chung and Raymond, 1993). Furthermore, in commercial production, high Lf concentration (10-20%) and low temperature are normally preferred for the iron release process, because lower temperature can prevent possible bacterial growth and higher concentration can be more efficient. Further, the inventors have found that when a lower temperature (2-12° C.) and a lower pH<3.5 are used, an Lf gel and precipitate may be formed.

In contrast, the inventors have now found that adding appropriate amount of a water miscible solvent (preferably an alcohol solvent) assists the iron release at moderate pH (<4.5), also it can assist in preventing precipitation or gelling. As a result an iron content of less than 14 mg/100 g iron or 10% iron saturation can be achieved. Surprisingly, the final product has a greatly improved antimicrobial activity, which cannot be explained by iron removal alone.

Lf has anti-microbial activity due to its ability to bind iron essential for the growth of certain bacteria. Some researchers (Bishop et al. 1976; Korhonen, 1977; Payne et al. 1990) reported that the antimicrobial activity of Lf depends on its iron saturation. Batish et al. (1988) found that the antibacterial activity of low-iron Lf is greater than that of Lf and this has been confirmed by others. Lf also has bactericidal activity by binding to lipopolysaccharides (LPS) on bacterial membranes to disrupt the cell wall (Ellison at al. 1988; 1990 and 1991; Yamauchi 1993 at al.).

It has now been found (refer to Tables 2, 3, and 4, especially Table 4, below) that both the low-iron Lf and standard Lf effectively killed a range of both Gram-negative and Gram-positive bacteria. However the low-iron Lf of the present invention exceeded the expected improvement in anti-microbial activity from its original Lf form Without wishing to be held to any particular hypothesis, the inventors postulate that the increased antimicrobial activity could be in part due to the Lf disrupting the outer membrane rather than solely by its iron binding activity.

Previous research has shown that both human and bovine Lfs cause the release of structural LPS and an increase in killing of bacteria (Ellison et al. 1988; 1990 and 1991; Yamauchi et al. 1993). Ellison at al. (1991) reported that human Lf has an ability to directly interact with the membrane and bind to LPS molecules. Later, Yamauchi et al. (1993) found that bovine Lf shares this property. They also indicated that bovine Lf alters the structure of the Gram-negative bacterial outer membrane to release LPS and kill the bacteria.

To review the hypothesis of LPS involvement the inventors determined the level of LPS release from bacteria exposed to the low-iron Lf and standard Lf (refer to FIG. 1). A positive correlation between Lf induced LPS release from the bacteria and Lf induced bacterial killing suggests that the ability of the Lf to release LPS from the bacteria is the key factor behind the improved anti-microbial activity rather than iron sequestration. This is reinforced by the observation that the killing ability of two low-iron Lf with different iron saturations (5.1 and 8.7%) and with different iron saturation reductions (7.9 and 3.5%) was similar, but much stronger than their original form (refer to Table 4).

Although the exact causes remain unclear, the improved antimicrobial activity shown by the low-iron Lf of the present invention could be due the above mechanisms or some other, as yet undetermined process.

To release the iron from Lf, a physiologically acceptable iron-chelating acid, or a combination of such acids (the suitable acid), is added with good mixing to a tank containing aqueous Lf preparation, preferably at a suitable temperature (typically about 8 to about 25° C.), to give the required pH. The change in absorbance at a wavelength of 465 nm is used to monitor the release of iron.

The iron release is closely correlated to the water-soluble iron chelators and pH. In a preferred reaction mixture, the Lf solution is mixed with the physiologically acceptable acid or a combination of such acids (as acid agent/s and chelator/s), such as citric acid, tartaric acid, oxalic acid, or ethylenediamine tetraacetic acid (EDTA), and preferably food grade, or a combination of the salts of these acids (e.g. sodium citrate or potassium citrate) with other physiologically acceptable organic or inorganic acids (e.g. HCl, $H_2SO_4$, acetic acid, etc). The most preferred option is to use citric acid only.

The concentration of acid added should be from about 0.1 to about 55%, preferably 5-20%, most preferably to about 10%. If the acid concentration is too high it may denature the Lf before mixing is complete. On the other hand, if acid concentration is too low, an inconveniently large volume of acid solution will be needed, which will dilute the Lf. The acid should preferably be added slowly with good mixing to avoid locally high concentrations that may denature the Lf.

The amount of iron released increased with decreasing pH below 7. Most of the iron released was from about pH<4.5. Furthermore, at about pH 3.8-4.5 the iron release is relatively slow and at pH<3.5 the iron release is much faster. In two cases, at higher pH you will use less acid but longer time whereas lower pH more acid is needed but short running time. However, low-iron Lf made at about the mild pH 3.8-4.5 has a much higher antimicrobial activity than its lower pH counterpart does. Therefore, the preferred pH is lowered to a range of between about 2.5-about 4.5 and preferably about 3.8-about 4.5, most preferred about 3.9-about 4.2.

A low-colour Lf solution containing ethanol and citric acid was diluted 1 to 5 in pure water and the pH was adjusted. The absorbance at 465 nm of the various solutions at room temperature was monitored. Typical results are shown in FIG. 2. This shows how the iron release is affected by different pH levels. The preferred pH is less than about 4.5.

The water miscible solvent (preferably an alcohol solvent) is added to assist in prevention of denaturation and precipitation of the Lf by acid and to also to assist in the promotion of iron release.

An appropriate amount water miscible solvent promotes iron removal at a moderate pH (about 3.8-4.5) and prevents the development of the turbidity or gelling in the Lf solutions at a lower pH of about 2.5-3.5. The water miscible solvent (preferable ethanol) should preferably be added before the acid. The amount of ethanol used is preferably between about 0.2 and about 2.5% in the Lf preparation, more preferably about 0.5-about 1.5%, the most preferably about 1%.

In addition to pH, and a sufficient amount of citric acid (or other suitable acid, preferably food grade), the iron release is closely correlated to the reaction time. Iron release increased with increasing mixing time until it reaches equilibrium. Because there is an inverse relationship between acid addition and reaction time, the higher the amount added (lower pH) the less time used to achieve targeted iron release. However, the addition of acid is limited by the pH, so if mixing a pure Lf product with a sufficient amount of citric acid, a period of contacting time can be from about 10 minutes to about 3 days to release the iron. In a typical processing, it is preferably about 3 minutes to about 24 hours, more preferably about 30 minutes to about 12 hours, most preferably about 6 to about 8 hours.

In addition to the process conditions, the quality of the Lf is important. For instance, in most commercial Lf preparations the level of impurities is about 4 to about 10% and denaturation is in the order of 10-25%. Consequently, the level of impurity and denaturation of Lf will affect the final product, so choice of the starting Lf is important and the use of suitable quality Lf is preferred. Skilled technical staff can determine the quality of the Lf.

The Lf used as starting product in the process according to the invention may be prepared in any conventional way. The starting Lf can be from colostrum, skim milk and whey of human, bovine or other mammal and is isolated by any conventional method, such as by chromatograph, ion-exchanger and molecular-sieve from laboratory and commercial available Lf. The Lf can be in either liquid (solution) or solid (powder) forms.

Mixtures of Lf and additives are formed by adding the additives (water miscible solvent, suitable acid) into the appropriate aqueous Lf preparation. The Lf concentration in the initial mixture is preferably not more than about 35%, preferably between about 0.01 to about 35% wt/vol, more preferably between about 5 to about 25% wt/vol, and most preferably between about 10 and about 20% wt/vol.

In a typical process, once the targeted iron release is achieved (<about 14 mg/100 g iron or about 10% iron saturation, more preferably <7 mg/100 g iron or 5% iron saturation), the iron released and process aids (acid and solvent) added are removed by using UF and/or DF or any other suitable technique.

Removing the Iron and Processing Aids

The iron released from Lf by citric acid (or other suitable acid) and alcohol (or other water miscible solvent) is readily taken up again if the pH of the mixture is restored to near neutral (refer to FIG. 3). The iron can therefore be removed using a desalting process, such as UF and/or DF or similar means, before pH neutralization and further processing of the Lf is attempted.

As Lf can release bound iron in a fully reversible manner, the iron and chemicals should be removed, by UF and/or DF (for example), to prevent the iron from rebinding during subsequent processing.

One Lf molecule binds two $Fe^{3+}$ ions with very high affinity. The iron-Lf complexes are stable at pH>3.5 in the absence of chelators. After the iron release described above, the key requirement for the iron removal from Lf solution by UF and DF seems to be the presence of citric acid (citrate), or other suitable acid, at sufficiently low pH, because it acts as a chelator and a pH controller. As observed by the inventors, the iron released can rebind back to the Lf when pH is increased (refer to FIG. 3). The pH should therefore preferably remain low until more than 90% of the released iron has been removed. The sufficiently low pH of Lf solution is preferably between about 3.8 and about 4.5, most preferably about 3.9-4.2. In FIG. 3, the samples were treated with the process aids (1% ethanol and pH to 4.0, 4.2, 4.3, 4.45, 4.75, 5.0, 5.35 and 5.8 respectively), placed in a 96 wells micro plate, and incubated in room temperature 22° C. The absorbances were measured at 0, 30, 60, 90, 120, 150 and 960 min. This shows the iron rebinding back to Lf at different pH, which can affect the final product iron saturation.

High quality water should preferably be used for DF to avoid contamination of the Lf. Most importantly, the iron content of water should preferably be low, preferably <about 0.2 ppm and most preferably <about 0.1 ppm. The water should also be free from traces of tannin and endotoxins.

The degree to which $Fe^{3+}$ ions and chemicals (citric acid and ethanol) in the Lf mixture are removed by the above mentioned desalting processes, e.g. by UF, may also result in pH changes, so should be closely monitored (correction of the pH to preferably about 4.2 of the treated Lf if outside the preferred pH range of about 4.0 to about 4.6 by using acid/alkali may be needed).

In a typical UF process, the process aids are added with agitation and allowed to react. When the reaction is complete the UF process is started. Water is added to help remove the released iron and the process aids that were added. There are two advantages to use UF before DF. Firstly, by using UF, much greater volume water can be added and removed than using DF, which should help to remove the iron and additives more quickly. Secondly, pH can be easily controlled with UF process. The removal of iron and additives can be monitored and when more than 90% of the iron is removed and the appropriate concentration of Lf achieved, the DF will start. Hence, appropriate concentration of Lf is achieved for the subsequent drying process.

Conversion of Lf to valuable low-iron Lf with improved bioactivity, together with suitable sensory and storage properties is often preferred for a commercial product. In order to obtain such a material the Lf is purified using DF where most impurities (mainly the process aids added) are removed. The DF step is primarily removing the acid and water miscible solvent added rather than iron and the Lf solution is diafiltrated to pH about 5.0. Depending on the kinds of final products desired, the pH can be up to 5.5-6.5 and conductivity 2 mS/cm by DF or adding alkali. If a good sensory product is desired, the Lf may be diafiltrated to a pH of 5.5-6.5. However, if the sensory property is not critical, the pH can be adjusted to the pH 5.5-6.5 with a food grade alkali, such as, KOH, NaOH or similar, or a mixture of several alkalis, preferably including NaOH. The alkali can be directly added into the solution but is preferably dissolved to 0.1-50%, preferably 1-10%, most preferably to about 2.5%.

High quality water should preferably be used for the DF to avoid contamination of the Lf. The iron content of water should be low, preferably <0.2 ppm and most preferably <0.1 ppm. The water should also be free from traces of tannin and endotoxins as Lf has a high affinity for these.

Once the processing is complete, the low-iron Lf can be freeze or spray dried and packed.

The process of the present invention can produce a low-iron Lf at a mild pH (3.8-4.5). Furthermore, a lower pH<3.5 can also be used, because the process can effectively reduce/prevent Lf denaturation as well. In addition to above, surprisingly and importantly, the final low-iron Lf product has a greatly improved antimicrobial activity. The invention therefore extends to that low-iron Lf that exhibiting improved anti-microbial properties.

Low-iron Lf can be used in a number of products such as infant formulas, nutritional formulations, immune enhancement products, oral care products and anti-acne products. In such uses, the improved anti-microbial activity helps to reduce harmful pathogens thus improving the quality and/or efficacy of the products. In particular, as low-iron Lf strongly binds to endotoxin—LPS the products can also assist the immune system of the user. The invention therefore extends to improving the anti-microbial qualities of products that incorporate (or could incorporate) an Lf component, by replacing use of standard Lf in those products, at least in part, with low iron Lf.

EXAMPLES

Example 1

Treatment of Lactoferrin with Various Reagents

Aliquots of 6% aqueous Lf solution containing 1% ethanol were treated with various reagents at pH 4.0 and 25° C. and the change in absorbance at 465 nm was monitored. Typical results are shown in Table 1.

Example 2

Preparation Low-Iron Lf at Laboratory Scale 20, 15, 10 and 5% solutions were reconstituted from commercial Lf. After 5 mL of 20% ethanol was added into 100 mL of above Lf samples, the pH of the Lf samples was adjusted to 4.0. The samples were stood at 20° C. for 16 hours to release $Fe^{3+}$. The iron release was monitored by measuring absorbance at 465 nm with a spectrophotometer. After 16 hours reaction, the samples were dialysed against pure water or tap water at a ratio of 1:20. After dialysis for two days with three changes of water daily, the samples were freeze-dried. The resulting products were either white in colour when made with pure water (3.89% iron saturation by HPLC and 4.03% by X-ray fluorescence (XRF)) or light cream or pale beige in colour when made with tap water (3.97% iron saturation by HPLC and 4.08 by XRF). All the resulting products are easily distinguishable from conventional Lf (salmon pink in colour). Iron rebinding results indicate that the low-iron Lf have not lost any iron binding ability. Antimicrobial results show that Lf dialysed with pure and tap water have similar antimicrobial activities but much stronger than conventional Lf. (refer to Table 5).

Example 3

Preparation Low-Iron Lf in a Commercial Plant Scale

After 50 L of 20% ethanol was added into 1000 L of 15% Lf, the pH of the Lf solution was adjusted to 4.1. The solution was slowly agitated to release $Fe^{3+}$ at 20° C. until the targeted $Fe^{3+}$ release achieved (16 hours) and then $Fe^{3+}$ released and process aids added were removed by UF and DF process. The resulting product is a light cream/pale beige colour with 5.1% saturation (by HPLC) and is easily distinguishable from conventional Lf. Iron rebinding results indicate that the low-iron lactoferrin has not lost any of its iron binding ability. Antimicrobial results show that it has an improved antimicrobial activity. (Refer to Tables 2 and 3.)

Iron Saturation Test

The ability of lactoferrin preparations to bind iron was determined by adding an excess of freshly made $FeCl_3$ solution to solutions of the test lactoferrin (2%) in 70 mM sodium bicarbonate solution (pH 7). The iron content of the resulting Lf was determined using cation exchange HPLC. The Lf was eluted off the column using a salt gradient with simultaneous determination of absorbance at 280 and 465 nm. The effect of iron on the 280 nm absorbance was recognised when determining the Lf concentration. XRF was used to confirm the HPLC assay.

Antimicrobial Activity

Suspensions of selected organisms were used to challenge the antimicrobial activity of various lactoferrin solutions as follows.

a) A single colony of *E. coli* (NZRM-916), *K. pneumoniae* (NZRM-7441), *B. cereus* (NZRM-5) or *S. aureus* (NZRM-87) isolated from a tryptic soy agar (TSA) plate was inoculated in 10 mL of tryptic soy broth (TSB) and incubated over night at 37° C.

b) Aliquots (100 µL) of the resulting $10^5$-$10^6$ cfu/mL cultures were added to 1 mL portions of Lf test solutions containing, in the first experiment 0.4% and 0.8% Lf, and in the second experiment (*E. coli* and *K. pneumoniae* only) 0.5%, 0.25 and 0.15% Lf. The mixtures were incubated at 37° C.

c) Samples (1 mL) of the incubating mixture were taken at 2 min, 30 min, 4 h and 24 h and placed into tubes containing 9 mL sterilised water. Further decimal (1 into 9 mL) dilutions were carried out using sterilised water as required to bring the cell numbers into the range $10^4$-$10^5$ cfu/mL.

d) 1 mL of the diluted samples were transferred in duplicate to Petri dishes, mixed with molten agar, and incubated for 24-48 h.

e) The colonies were then counted.

The results are shown in Tables 1, 2, 3, 4 and 5. The low-iron Lf acted more quickly and at lower concentrations than the control Lf.

LPS Release

Lf antimicrobial activity mainly involves following two known mechanisms: one is iron-depriving activity due to its high affinity to iron; another is its ability to bind to bacterial membrane to release LPS from the bacteria membrane to make the membrane more permeable to kill the bacteria (especially Gram-negative). The ability of Lf to bind to bacteria and to release LPS from the membrane appears to be related to its direct bactericidal activity. The low-iron Lf according to the present invention has a greatly improved antimicrobial activity in comparison to standard Lf that cannot be explained by the reduction in iron content (such low-iron Lf forming an inventive aspect of the present invention), so it is important to determine if the greatly improved antimicrobial activity is due to binding to cell membrane and release LPS.

The release of LPS from selected organisms due to exposure to Lf was determined as follows.

a) A few colonies of *E. coli* (NZRM-916) or *K. pneumoniae* (NZRM-7441) isolated from a tryptic soy agar (TSA) plate were inoculated into 180 mL of tryptic soy broth (TSB) and the broth was incubated at 37° C. over night.

b) Cells were harvested by centrifuging the culture in 50 mL centrifuge tubes at 1000 g for 10 min. The resulting pellet was dispersed in pure water and centrifuged again.

c) The washed pellets were mixed with 40 mL of 0.8% Lf solutions and incubated at 37° C.

d) Samples were taken 0 and 30 min. and centrifuged in 50 mL centrifuge tubes at 1000 g for 10 min. The resulting clear supernatant was mixed with 3 volumes of 99% ethanol. The resulting precipitate was recovered by centrifuging at 1000 g for 10 min.

e) The pellet was dissolved with 10 mL pure water and centrifuged again the supernatant was dialysed against pure water at a ratio of 1:100 for two days, with two changes of water daily.

f) The dialysed samples were analysed with the phenol-sulphuric acid assay (Dubois et al, 1956). Glucose was used as standard to quantify the LPS. Time 0 samples were used as blanks.

The results are shown in FIG. 1. As can clearly be seen, the anti-microbial activity of the low-iron Lf is significantly, and surprisingly, greater than that of standard Lf. This finding is supported by the results shown in the other tables (and referred to above) that the low-iron Lf acted more quickly and at lower concentrations than the control Lf.

Tables

TABLE 1

Changes in absorbance at 465 nm when alcoholic lactoferrin solution is treated with various acids.

| Time (min) | Control | Gluconic acid | Tartaric acid | EDTA + HCl | Oxalic acid | Citric acid |
|---|---|---|---|---|---|---|
| 10 | 0.387 | 0.317 | 0.312 | 0.259 | 0.287 | 0.291 |
| 20 | | 0.314 | 0.292 | 0.219 | 0.203 | 0.260 |
| 40 | | 0.312 | 0.281 | 0.220 | 0.132 | 0.247 |
| 80 | | 0.303 | 0.255 | 0.212 | 0.125 | 0.221 |
| 160 | | 0.297 | 0.246 | 0.193 | 0.124 | 0.189 |
| 230 | | 0.296 | 0.235 | 0.189 | 0.126 | 0.152 |
| 320 | | 0.288 | 0.241 | 0.183 | 0.131 | 0.141 |
| 450 | | 0.282 | 0.239 | 0.168 | 0.131 | 0.107 |
| 1200 | | 0.261 | 0.189 | 0.143 | 0.121 | 0.064 |

TABLE 2

Survival of bacterial after exposure to lactoferrin solutions

| Bacteria | Lactoferrin type | Lactoferrin conc. (%) | 2 min | 30 min | 4 h | 24 h |
|---|---|---|---|---|---|---|
| E. coli | Low-iron | 0.4% | 14 | <1 | <1 | <1 |
| | | 0.8% | <1 | <1 | <1 | <1 |
| | Standard | 0.4% | TNTC | 858 | <1 | <1 |
| | | 0.8% | TNTC | 264 | <1 | <1 |
| S. aureus | Low-iron | 0.4% | TNTC | TNTC | TNTC | 1820 |
| | | 0.8% | TNTC | TNTC | TNTC | 750 |
| | Standard | 0.4% | TNTC | TNTC | TNTC | TNTC |
| | | 0.8% | TNTC | TNTC | TNTC | TNTC |
| K. pneumoniae | Low-iron | 0.4% | 45 | <1 | <1 | <1 |
| | | 0.8% | 5 | <1 | <1 | <1 |
| | Standard | 0.4% | TNTC | 635 | 352 | TNTC |
| | | 0.8% | TNTC | 479 | 311 | TNTC |
| B. cereus | Low-iron | 0.4% | 467 | 142 | 8 | 5 |
| | | 0.8% | 382 | 53 | 9 | 6 |
| | Standard | 0.4% | TNTC | TNTC | 526 | 697 |
| | | 0.8% | TNTC | TNTC | 439 | 321 |

(TNTC = too numerous to count).

TABLE 3

Survival of bacterial after exposure to lactoferrin solutions

| Bacteria | Lactoferrin Type | Lactoferrin conc. (%) | 2 min | 30 min | 4 h | 24 h |
|---|---|---|---|---|---|---|
| E. coli | Low-iron | 0.50 | 162 | <1 | <1 | <1 |
| | | 0.25 | 988 | <1 | <1 | <1 |
| | | 0.15 | 2306 | 49 | <1 | <1 |
| | Standard | 0.50 | TNTC | 2113 | <1 | <1 |
| | | 0.25 | TNTC | TNTC | 2557 | 478 |
| | | 0.15 | TNTC | TNTC | TNTC | TNTC |
| K. pneumoniae | Low-iron | 0.50 | 1353 | 211 | <1 | <1 |
| | | 0.25 | 3685 | 639 | <1 | <1 |
| | | 0.15 | TNTC | 2276 | 6 | <1 |
| | Standard | 0.50 | TNTC | 4611 | 19 | <1 |
| | | 0.25 | TNTC | TNTC | 2557 | 1661 |
| | | 0.15 | TNTC | TNTC | TNTC | TNTC |

(TNTC = too numerous to count).

TABLE 4

Survival of bacterial after exposure to different iron saturation lactoferrin solutions

| Bacteria | Lactoferrin type | Lactoferrin Iron saturation. (%) | 2 min | 30 min | 4 h | 24 h |
|---|---|---|---|---|---|---|
| E. coli | Low-iron Lf 1 | 5.1 | 354 | 21 | <1 | <1 |
| | Low-iron Lf 2 | 8.7 | 14 | <1 | <1 | <1 |
| | Parent of Low-iron Lf 1 | 13 | TNTC | 956 | 337 | <1 |
| | Parent of Low-iron Lf 2 | 12.2 | TNTC | 858 | <1 | <1 |
| K. pneumoniae | Low-iron Lf 1 | 5.1 | 31 | <1 | <1 | <1 |
| | Low-iron Lf 2 | 8.7 | 45 | <1 | <1 | <1 |
| | Parent of Low-iron Lf 1 | 13 | TNTC | 55 | 116 | 529 |
| | Parent of Low-iron Lf 2 | 12.2 | TNTC | 635 | 352 | TNTC |

(TNTC = too numerous to count).

TABLE 5

Survival of bacterial after exposure to lactoferrin (UF & DF with different water) solutions

| Bacteria | Lactoferrin | Lactoferrin made from water type | 2 min | 30 min | 4 h | 24 h |
|---|---|---|---|---|---|---|
| E. coli | Low-iron | Tap | 9 | <1 | <1 | <1 |
| | | Pure | 38 | <1 | <1 | <1 |
| | Standard | | TNTC | 2892 | 314 | <1 |

(TNTC = too numerous to count).

The forgoing describes the invention including preferred forms thereof. Alterations and modifications that would be readily apparent to the skilled person are intended to be included within the scope of the invention as defined in the attached claims.

REFERENCES

Aisen P, Leibman A. (1972). Lactoferrin and transferrin: a comparative study. Biochim. Biophys. Acta 257 (2) 314-323.

Batish V K, Chander H, Zumdegni K C, Bhatia K L, Singh R S. (1988). Antibacterial activity of Lf against some common food-borne pathogenic organisms. Aust. J. Dairy Technol. 43 (1) 16-18.

Bishop J G, Schanbacher F L, Ferguson L C, Smith K L. (1976). In vitro growth inhibition of mastitis-causing coliform bacteria by bovine apo-lactoferrin and reversal of inhibition by citrate and high concentrations of apo-lactoferin. Infect Immun. 14 (4) 911-918.

Chung T D Y, Raymond K N. (1993). Lactoferrin: The role of conformational changes in its iron binding and release. J. Am. Chem. Soc. 115 (15) 6765-6768

Dubois M, Gilles K A, Hamilton J K, Rebers P A, Smith F. (1956). Colorimetric method for determination of sugars and related substances. Anal. Chem. 28 (3) 350-356.

Ellison R T 3rd, Giehl T J, LaForce F M. (1988). Damage of the outer membrane of enteric Gram-negative bacteria by lactoferrin and transferrin. Infect Immun. 56 (11) 2774-2781.

Ellison R T 3rd, LaForce F M, Giehl T J, Boose D S, Dunn B E. (1990). Lactoferrin and transferrin damage of the Gram-negative outer membrane is modulated by $Ca^{2+}$ and $Mg^{2+}$. J Gen Microbiol. 1990 July; 136(7):1437-46.

Ellison R T 3rd, Giehl T J. (1991). Killing of Gram-negative bacteria by lactoferrin and lysozyme. J Clin Invest. 1991 October; 88(4):1080-91.

Feng M, van der Does L, Bantjes A. (1993). Iron(III)-chelating resins. 3. Synthesis, iron(III)-chelating properties, and in vitro antibacterial activity of compounds containing 3-hydroxy-2-methyl-4(1H)-pyridinone ligands. J. Med. Chem. 36 (19) 2822-2827.

Feng M, van der Does L, Bantjes A. (1995). Preparation of apolactoferrin with a very low-iron saturation. J. Dairy Sci. 78 (11) 2352-2357.

Franken K L, Hiemstra H S, van Meijgaarden K E, Subronto Y, den Hartigh J, Ottenhoff T H, Drijfhout J W. (2000). Purification of his-tagged proteins by immobilized chelate affinity chromatography: the benefits from the use of organic solvent. Protein Expr Purif. 18 (1) 95-99.

Groves M L. (1960). The isolation of a red protein from milk. J. Am. Chem. Soc. 82 (13) 3345-3350.

Kontoghiorghes G J. (1986). Iron mobilization from lactoferrin by chelators at physiological pH. Biochim. Biophys. Acta 882 (2) 267-270.

Korhonen H. (1977). Antimicrobial factors in bovine colostrum. Journal of the Scientific Agricultural Society of Finland 49 (5) 434-447.

Kretchmar Nguyen S A, Craig A, Raymond K N. (1993). Transferrin: the role of conformational changes in iron removal by chelators. J. Am. Chem. Soc. 115 (15) 6758-6764.

Law B A, Reiter B. (1977). The isolation and bacteriostatic properties of Lactoferrin from bovine milk whey. J. Dairy Res. 44 (3) 595-599.

Magalhaes P O, Lopes A M, Mazzola P G, Rangel-Yagui C, Penna T C, Pessoa A Jr. (2007). Methods of endotoxin removal from biological preparations: a review. J Pharm Pharm Sci. 10 (3) 388-404.

Masson P L, Heremans J F. (1968). Metal-combining properties of human lactoferrin (red milk protein). 1. The involvement of bicarbonate in the reaction. European J. Biochem. 6 (4) 579-584.

Mazurier J, Spik G. (1980). Comparative study of the iron-binding properties of human transferrins. I. Complete and sequential iron saturation and desaturation of the lactotransferrin. Biochim. Biophys. Acta 629 (2) 399-408.

Naidu A S. (2001). Immobilized lactoferrin antimicrobial agents and the use. U.S. Pat. No. 6,172,040.

Naidu A S. (2006). Treatments for contaminant reduction in lactoferrin preparations and lactoferrin containing compositions. U.S. Pat. No. 7,125,963.

Naidu A S. (2008). Treatments for contaminant reduction in lactoferrin preparations and lactoferrin-Containing compositions. U.S. Pat. No. 7,326,775.

Payne K D, Davidson P M, Oliver S P, Christen G L. (1990). Influence of bovine lactoferrin on the growth of Lysteria monocytogenes. J. Food Prot. 53 (6) 468-472.

Petsch D, Anspach F B. (2000). Endotoxin removal from protein solutions. J Biotechnol. 76 (2-3) 97-119.

Peterson N A, Anderson B F, Jameson G B, Tweedie J W, Baker E N. (2000). Crystal structure and iron-binding properties of the R210K mutant of the N-lobe of human lactoferrin: implications for iron release from transferrins. Biochemistry 39 (22) 6625-33.

Reiter B. (1985). Protective proteins in milk—biological significance and exploitation. Page 8-10 in IDF Bull. 191. Int. Dairy Fed, Brussels, Belgium.

Ropp P A, Murray M V. (2006). Removal of lipopolysaccharides from protein-lipopolysaccharide complexes by non-flammable solvents. United States patent application 2006 0189790.

Rowe G, Aomari H, Petitclerc D. (2006). New purification method of lactoferrin. Patent application WO2006 119644.

Ward L S, Thomson K, Wrobel S. (2009). United States patent application 2009 0029921. Method for removing endotoxin from proteins.

Yamauchi K, Tomita M, Giehl T J, Ellison R T 3rd. (1993). Antibacterial activity of lactoferrin and a pepsin-derived lactoferrin peptide fragment. Infect Immun. 1993 February; 61(2):719-28.

The invention claimed is:

1. A method for manufacturing low-iron lactoferrin (Lf) having improved antimicrobial activity from an aqueous Lf preparation, which comprises combining the aqueous Lf preparation with an alcohol solvent and a suitable acid such that the pH is between 2.5 and about 4.5 to release the iron from the Lf, and removing the released iron, alcohol solvent and acid.

2. The method according to claim 1 wherein the suitable acid is selected from any one or more of citric acid, tartaric acid, oxalic acid, nitrilotriacetic acid, or EDTA.

3. The method according to claim 1, wherein the suitable acid is citric acid.

4. The method according to claim 1, wherein the suitable acid can be formed from a citric acid salt and one or more organic or inorganic acid.

5. The method according to claim 1, wherein the suitable acid can be formed from a citric acid salt and an acid selected from HCl, $H_2SO_4$, or acetic acid.

6. The method according to claim 1, wherein the suitable acid is formed from sodium citrate or potassium citrate and one or more organic or inorganic acid.

7. The method according to claim 1, wherein the alcohol solvent is selected from methanol, ethanol, or propanol.

8. The method according to claim 1, wherein the released iron, alcohol solvent and acid are removed using ultrafiltration (UF) and/or diafiltration (DF).

9. The method according to claim 1 wherein the low-iron Lf produced contains less than about 14 mg/100 g iron or about 10% iron saturation.

10. A method for manufacturing low-iron Lf and with higher antimicrobial activity than normal commercial Lf, the method comprising:
   a) mixing an aqueous Lf preparation with an alcohol solvent and sufficient acid solution such that the pH is lowered to between about 2.5 to about 4.5 to release the iron from the Lf in the aqueous Lf preparation;
   b) removing the released iron, acid and alcohol by UF and/or DF to achieve a processing pH>about 5.5 and a conductivity <about 2 mS in the product;
   c) further processing the low-iron Lf product produced in (b) to produce a liquid or dried low-iron Lf product.

11. The method according to claim 10 wherein the low-iron Lf produced contains less than about 14 mg/100 g iron or about 10% iron saturation.

12. The method according to claim 10 wherein the low-iron Lf product in step c) is freeze-dried or spray-dried.

13. The method according to claim 10 wherein the acid is selected from citric acid, tartaric acid, oxalic acid, nitrilotriacetic acid, or EDTA.

14. The method according to claim 10 wherein the pH in step a) is lowered to between about 3.5 and about 4.5.

15. The method according to claim 12 wherein the aqueous Lf preparation in step a) is treated with acid solution for a period from about 2 hours to about 3 days to release the iron.

16. The method according to claim 10 wherein the concentration of the acid solution used in step a) is between about 5 to about 20%.

17. The method according to claim 10 wherein the alcohol solvent is added prior the addition of the acid.

18. The method according to claim 10 wherein the alcohol solvent is selected from any one or more of methanol, ethanol, propanol or similar alcohol.

19. The method according to claim 10 wherein the alcohol solvent is added in an amount of between about 0.2 and about 2.5% of the Lf preparation.

20. The method according to claim 10 wherein the processing pH is between about 3.5 and about 4.5.

21. The method according to claim 10 wherein the temperature in step a) is between about 2 and about 30° C.

22. The method according to claim 10 wherein the temperature in step b) is between about 5 and about 10° C.

23. The method according to claim 10 wherein the Lf in the aqueous Lf preparation is sourced from colostrum, skim milk or whey of bovine, human or other mammals.

24. The method according to claim 10 wherein the Lf in the aqueous Lf preparation is isolated by chromatograph, ion-exchanger and molecular-sieve means.

25. The method according to claim 10 wherein the Lf in the aqueous Lf preparation can be an undried extract or solution, or a dried powder.

26. The method according to claim 10 wherein the concentration of Lf in the aqueous Lf preparation is between about 0.01 and about 35% wt/vol.

\* \* \* \* \*